(12) United States Patent
Keilman et al.

(10) Patent No.: US 7,872,613 B2
(45) Date of Patent: Jan. 18, 2011

(54) ENHANCED IMPLANTABLE HELICAL ANTENNA SYSTEM AND METHOD

(75) Inventors: George W. Keilman, Bothell, WA (US); Timothy Johnson, Bothell, WA (US)

(73) Assignee: Pacesetter, Inc., Sylmar, CA (US)

( * ) Notice: Subject to any disclaimer, the term of this patent is extended or adjusted under 35 U.S.C. 154(b) by 386 days.

(21) Appl. No.: 12/060,816

(22) Filed: Apr. 1, 2008

(65) Prior Publication Data

US 2009/0243956 A1    Oct. 1, 2009

(51) Int. Cl.
*H01Q 1/36* (2006.01)
(52) U.S. Cl. .................. 343/895; 343/873; 128/899
(58) Field of Classification Search .......... 343/873, 343/895; 128/899, 903; 607/60, 156
See application file for complete search history.

(56) References Cited

U.S. PATENT DOCUMENTS

| | | | |
|---|---|---|---|
| 6,515,626 B2* | 2/2003 | Bark et al. | 343/700 MS |
| 7,375,699 B2* | 5/2008 | Forster et al. | 343/806 |
| 2008/0094308 A1* | 4/2008 | Cowles | 343/895 |

* cited by examiner

*Primary Examiner*—Tan Ho

(57) ABSTRACT

As described herein vascular anchoring systems are used to position an implant in a vascular area such as a bifurcated vasculature with relatively high fluid flow, for instance, in an area of a pulmonary artery with associated left and right pulmonary arteries. Implementations include an anchoring trunk member having a first anchoring trunk section and a second anchoring trunk section. Further implementations include a first anchoring branch member extending from the anchoring trunk member. Still further implementations include a second anchoring branch member extending from the anchoring trunk member.

20 Claims, 16 Drawing Sheets

US 7,872,613 B2

ENHANCED IMPLANTABLE HELICAL ANTENNA SYSTEM AND METHOD

BACKGROUND OF THE INVENTION

1. Field of the Invention

The present invention is generally related to antennas for implantable devices.

2. Description of the Related Art

Conventional implantable antennas can be constructed with a manner of accommodation with respect to incorporation into a body that is less than desirable. For instance, conventional antennas are found in enclosures, such as for heart pace makers, that require substantial room, which may be overly restrictive for other applications, such as vascular implantation.

BRIEF DESCRIPTION OF THE SEVERAL VIEWS OF THE DRAWING(S)

DETAILED DESCRIPTION OF THE INVENTION

As discussed herein, implementations of an enhanced implantable system and method include use of one or more pseudoelastic and/or superelastic materials (referred to herein as "p/s elastic") such as p/s elastic metal alloys, such as Nitinol, and/or p/s elastic polymers to provide at least a portion of the associated support structure for the implantable antenna. In implementations, the support structure has the general shape of the associated antenna either by one or more portions as integrated support structures being directly incorporated into the antenna structure typically as a tubular support structure and/or portions serving as a backbone support structure with a shape similar to the supported antenna components such as including inductive (H-field) and E-field antenna implementations discussed herein.

Use of p/s elastic material in the antenna support structure provides greater implantation adaptability and accommodation for the enhanced implantable antenna compared with conventional approaches. The p/s elastic materials used can have elastic response over large strains. For instance, when mechanically loaded, p/s elastic materials can deform reversibly even under strains, of up to approximately 6% to 10% so that the antenna structure will return to a desired shape after undergoing large strain levels. This large reversible elastic deformation capability provides relatively high flexibility to accommodate minimally invasive insertion into the body, and other implantation scenarios. Furthermore, pseudoelastic materials exhibit a stress plateau at larger strains, which is desirable for accommodating motion within the body and for minimizing the stress on tissues. FIGS. 1 through 6 illustrate various cross sectional views of antenna implementations that can be used with the implant versions shown in FIGS. 7 through 11.

Figure 1:
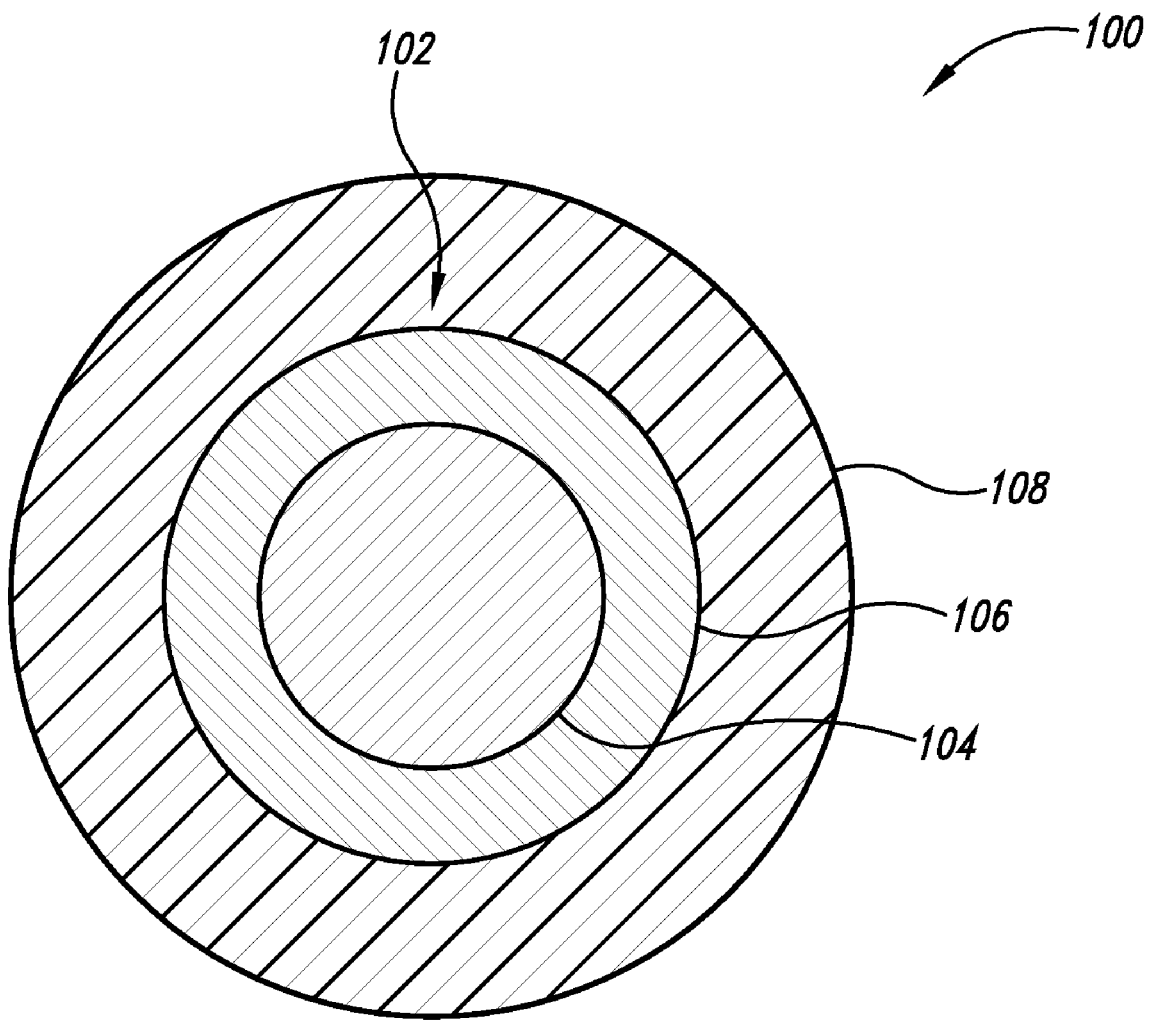
FIG. 1 is a sectional view of a first implementation of the enhanced implantable antenna system using a tubular support structure.

A first implementation 100 of the enhanced implantable antenna system incorporating tubular support is sectionally shown in FIG. 1 to include a coaxial set 102 of an electrically conductive core 104 filling a tubular support structure 106, which is further encased by an external electrical insulator 108. Versions of the coaxial set 102 that use a drawn filled tube (DFT) wire of p/s elastic material, such as Nitinol, for the tubular support structure 106 can serve both a support role and an antenna role for the enhanced implantable antenna system. Given the various biological environments (such as in and around vicinities of the heart) of the enhanced implantable antenna system, the p/s elastic material used for the tubular support structure 106 and other support structures discussed herein has long fatigue life (such as 1,000,000 cycles, 10,000,0001 cycles, 100,000,000 cycles, and/or 400,000,000 cycles for temperature ranges such as of at least between 33 degrees Celsius to 43 degrees Celsius or such as of at least between 0 degrees Celsius to 100 degrees Celsius)) to exist in areas such as inside of the heart.

Some versions of the enhanced implantable antenna system also use p/s elastic materials with high elasticity: some having an elastic strain level of approximately 3% or more and others having an elastic strain level of approximately 6% or more for temperature ranges such as of at least between 33 degrees Celsius to 43 degrees Celsius or such as of at least between 0 degrees Celsius to 100 degrees Celsius to provide flexibility to be collapsed or compressed to allow for temporary enclosure by delivery mechanisms, such as a catheter, a cannula, or other mechanical tubular structure of a delivery mechanism before being released to expand into an uncompressed state to be located in a vascular structure, other endoluminal tubular structure or biological tubular structure.

Since Nitinol is superelastic, it can be strained up to an elastic limit of about 6% without permanent deformation. Some P/S elastic materials, such as Nitinol, have an additional advantage in that they have shape memory properties, and can be "shape-set" to a desired geometry. In the case of Nitinol, the shape setting process requires holding the wireform in a desired geometry while undergoing a heat treatment at a temperature of approximately 500 degrees Celsius.

Due to the high shape-setting temperature, a Nitinol or Nitinol DFT antenna member requires shape setting prior to applying polymeric electrical insulation such as could be used for the external insulator 108. Several different insulation techniques are possible, including vapor deposition (e.g., Parylene), dip or spray coating (various polymers, either in the melt phase or prior to cross-linking), casting, injection molding, or by swelling a polymeric extrusion and sliding the shape-set wires into position. The latter technique is most easily accomplished using a silicone extrusion, which can be swelled in a liquid such as pentane, hexane, heptane, xylene, or a low molecular weight alcohol. The presence of the solvent in the silicone makes it particularly lubricious, allowing insertion of the wires with minimal force.

Like other p/s elastic materials, Nitinol and Nitinol DFT wires include another advantageous aspect. Nitinol has two crystalline states: martensite at low temperatures and austenite at higher temperatures. The transition temperature may be tailored by adjusting the metallurgical composition and processing that the material undergoes during manufacturing, to produce transition temperatures at, above, or below room temperature. In medical applications, the transition temperature can thus be set between room temperature (~20° C.) and body temperature (37° C.), so that a device transitions from its martensitic phase to its austenitic phase as it is introduced into the body. Only the austenitic phase is superelastic, whereas the martensitic phase is quite plastic.

In some implementations, p/s elastic material, such as Nitinol, can be processed as follows:
Shape-set the subject member, such as the coaxial set 102 and/or the tubular support structure 106, to the desired shape at approximately 500° C.
Cool the subject member to transition it into its martensitic phase
Straighten (or otherwise shape) the subject member to facilitate application of the insulating material, such as the external insulator 108
Apply insulating material, such as the external insulator 108 to the subject member
Implant final assembly steps can be completed with the subject member in either phase as required by other considerations.

Electrical resistivities of materials of interest are summarized below:

| Material | Resistivity MicroOhm-cm |
|---|---|
| Silver | 1.629 |
| Copper | 1.724 |
| Gold | 2.44 |
| Aluminum | 2.828 |
| Iridium | 5.29 |
| Brass | 7 |
| Nickel | 7.8 |
| Iron | 10 |
| Platinum | 10 |
| Tin | 10.9 |
| Steel | 11.8 |
| Lead | 22 |
| Nitinol SE 508 | 82 |
| Titanium | 55.4 |
| MP35N | 103.3 |
| PtIr | 25 |
| NiTi/Cu | 47.6 |

Figure 2:
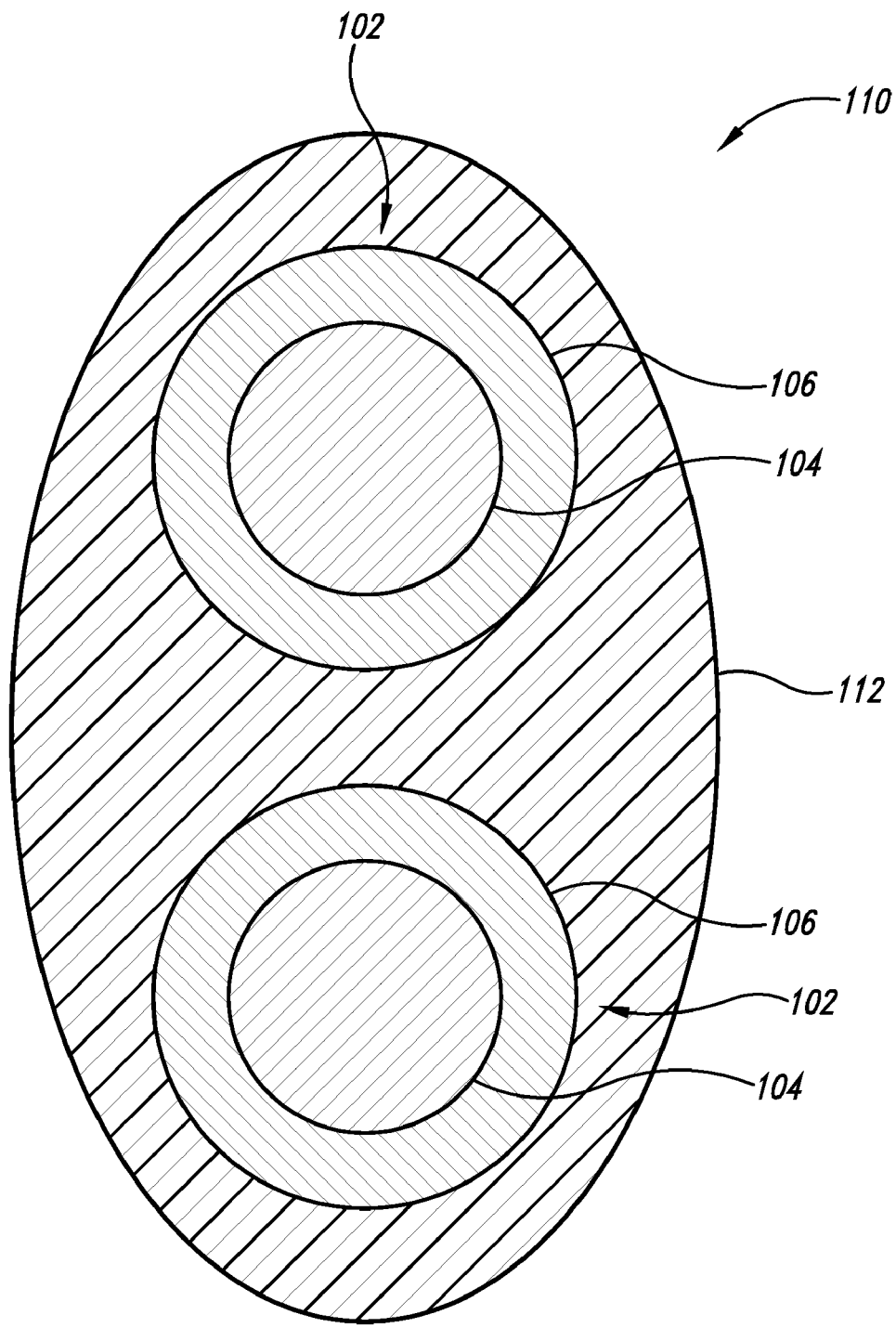
FIG. 2 is a sectional view of a second implementation of the enhanced implantable antenna system using the tubular support structure.

A second implementation 110 of the enhanced implantable antenna system is sectionally shown in FIG. 2 to include two of the coaxial sets 102 of the conductive core 104 and the tubular support structure 106 both encased in an external insulator 112.

Figure 3:
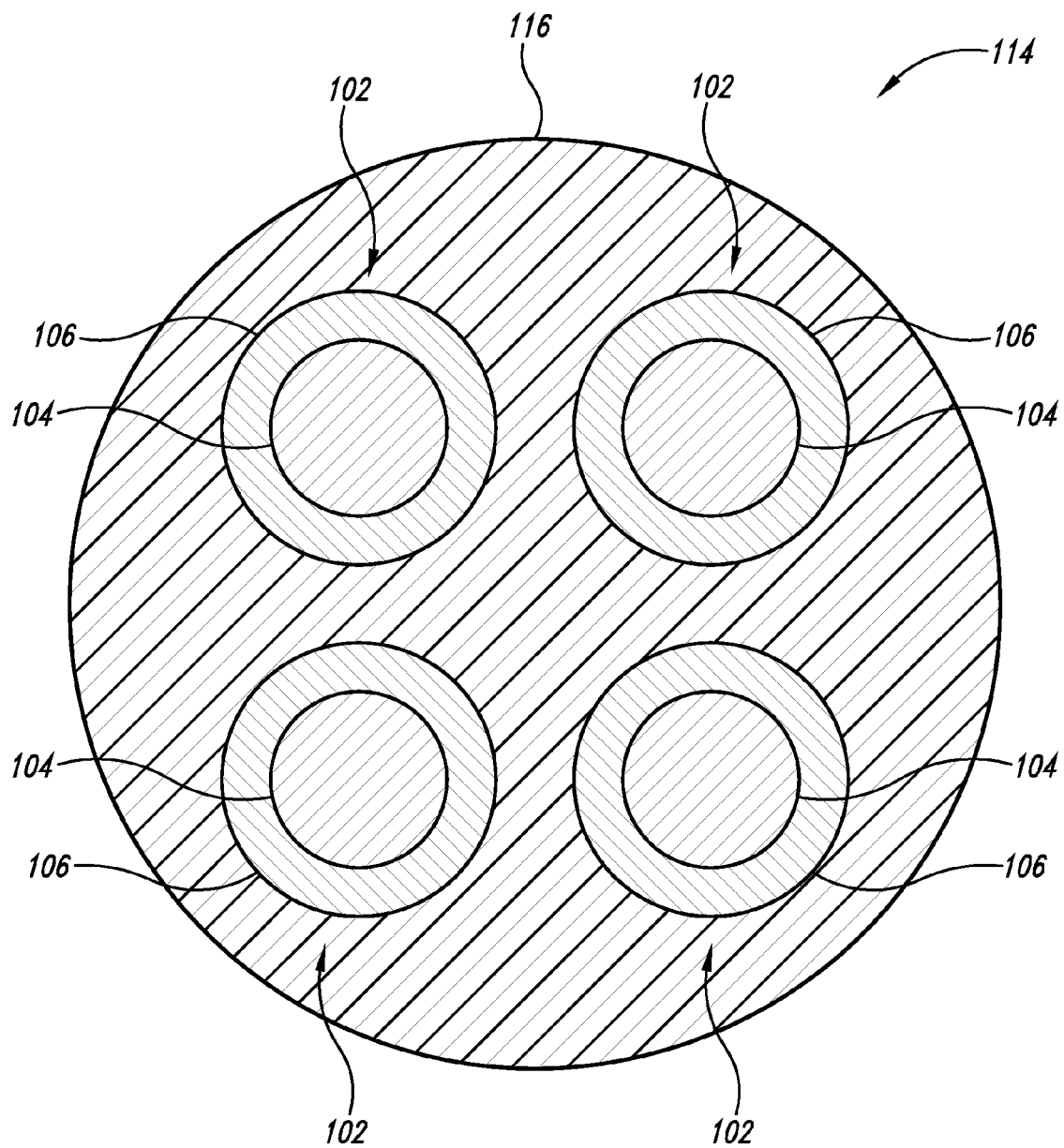
FIG. 3 is a sectional view of a third implementation of the enhanced implantable antenna system using the tubular support structure.

A third implementation 114 of the enhanced implantable antenna system is sectionally shown in FIG. 3 to include four of the coaxial sets 102 of the conductive core 104 and the tubular support structure 106 all encased in an external insulator 116. Any quantity of the coaxial set 102 can be put together in this fashion.

Figure 4:
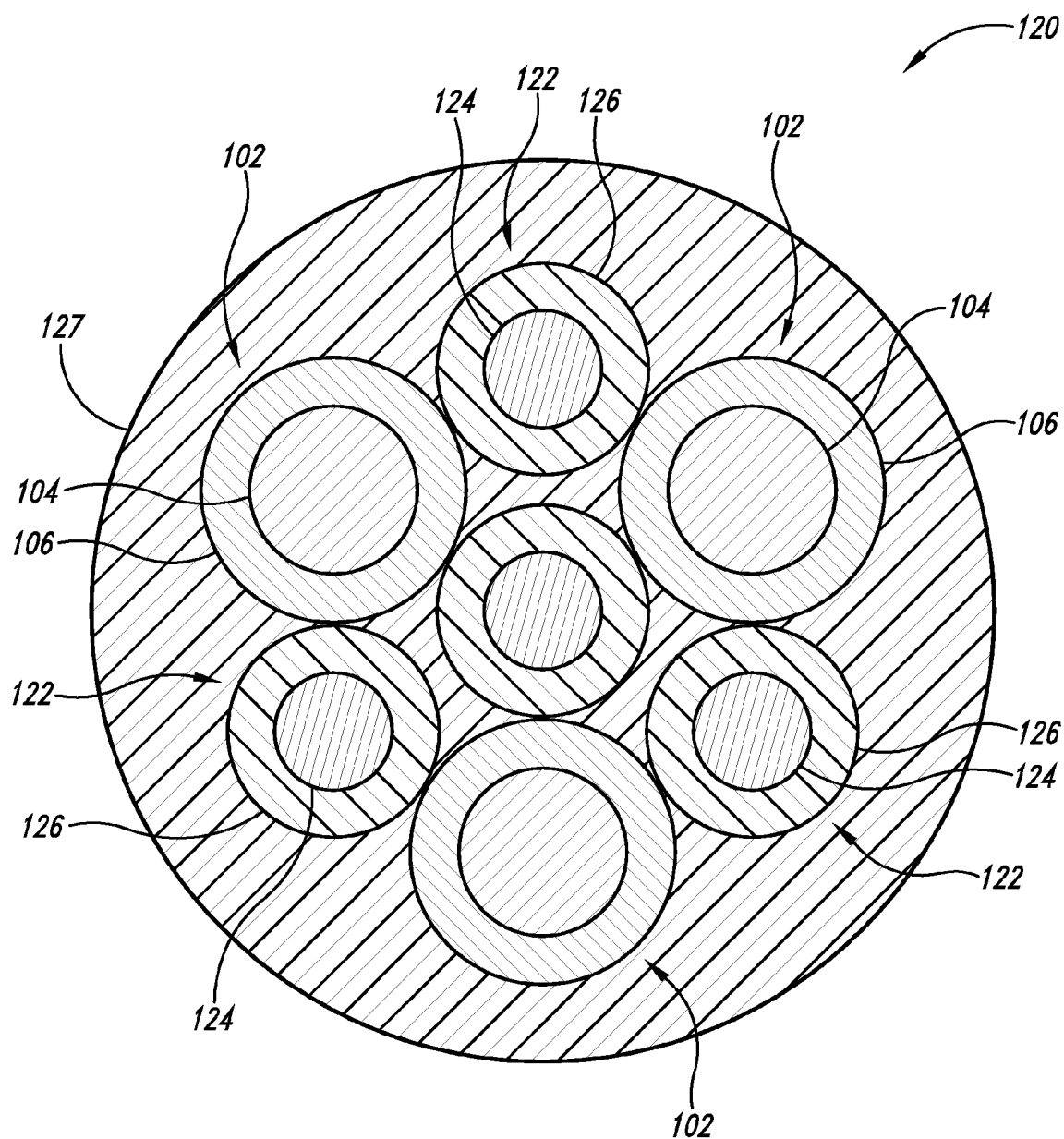
FIG. 4 is a sectional view of a fourth implementation of the enhanced implantable antenna system using the tubular support structure.

A fourth implementation 120 of the enhanced implantable antenna system is sectionally shown in FIG. 4 to include three of the coaxial sets 102 of the conductive core 104 and the tubular support structure 106 and insulated conductors 122 having an elongated conductive member 124 encased by an insulator 126. The three coaxial sets 102 and the four insulated conductors 122 are further encased in an insulator 127. The three coaxial sets 102 and the four insulated conductors 122 are shown in a symmetrical configuration, but other symmetrical or asymmetrical configurations can also be implemented in various other numbers of the coaxial sets and of the insulated conductors. Whereas other implementations can be made, given the implementation depicted in FIG. 4, one to three of the coaxial sets 102 and one to four of the insulated conductors 122 may be connected electrically in series or parallel to form an antenna configuration.

Figure 4A:
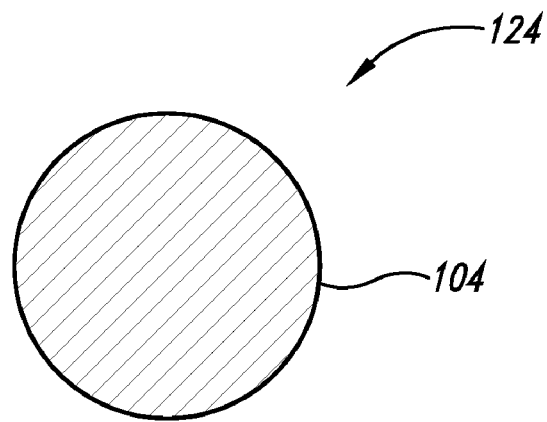
FIG. 4A is a sectional view of a conductive member as a solid conductor.
Figure 4B:
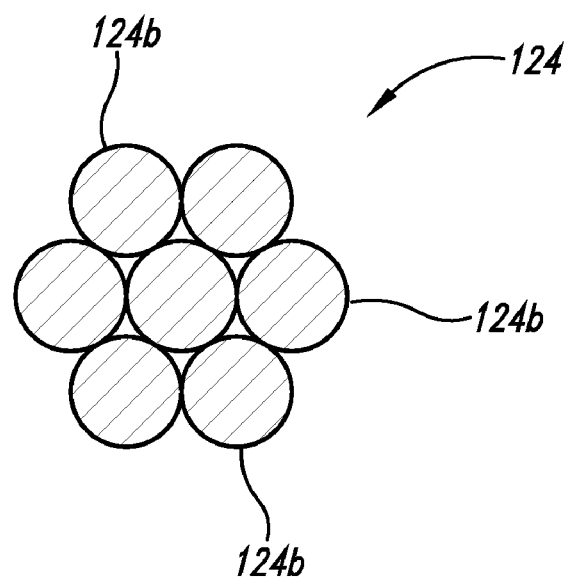
FIG. 4B is a sectional view of a conductive member as a bundle of stranded conductors.
Figure 4C:
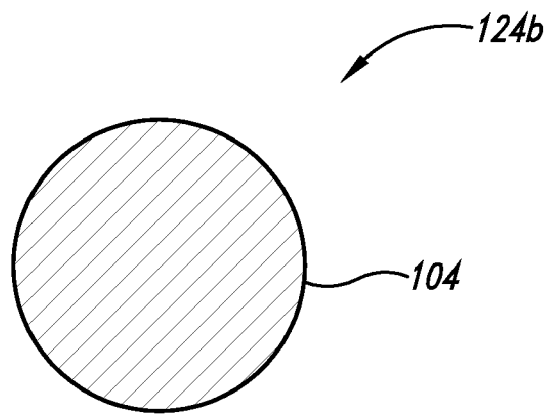
FIG. 4C is a sectional view of a stranded conductor as a solid conductor.
Figure 4D:
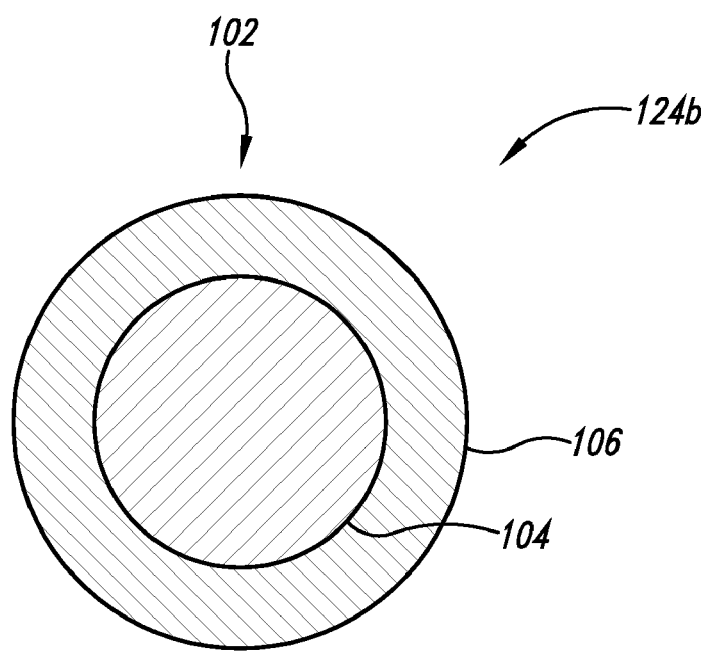
FIG. 4D is a sectional view of a stranded conductor as a coaxial set.

Each of the elongated conductive members 124 in some implementations are solid conductors as the conductive core 104 as shown in FIG. 4A. In other implementations, the elongated conductive members 124 are each a bundle of stranded conductors 124b such as shown in FIG. 4B. Each of the stranded conductors 124b can be solid core conductors such as smaller diameter versions of the conductive core 104 as shown in FIG. 4C or can be smaller diameter versions of the coaxial set 102 as shown in FIG. 4D or another type of drawn filled tube (DFT) wire or drawn brazed strand (DBS) wire with a conductive core. To maintain superelastic properties of the stranded wire, one or more of the strands would be chosen to contain Nitinol, either in solid, DFT, or other form.

Figure 4E:
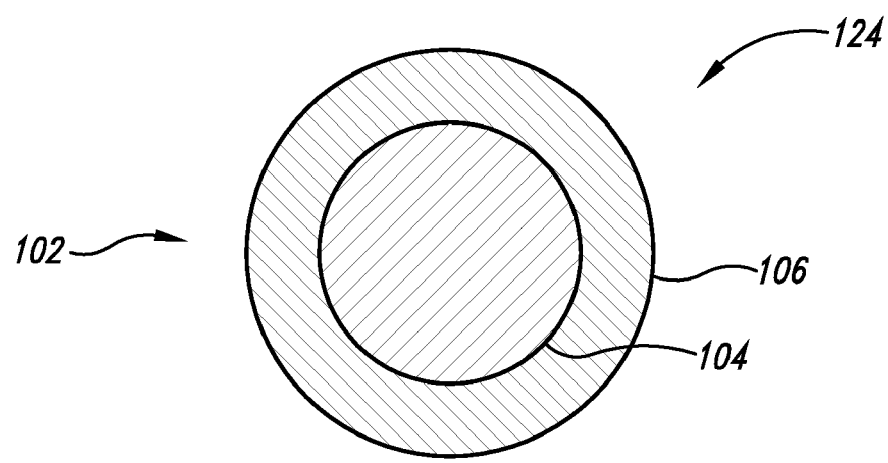
FIG. 4E is a sectional view of a conductor as a coaxial set.
Figure 4F:
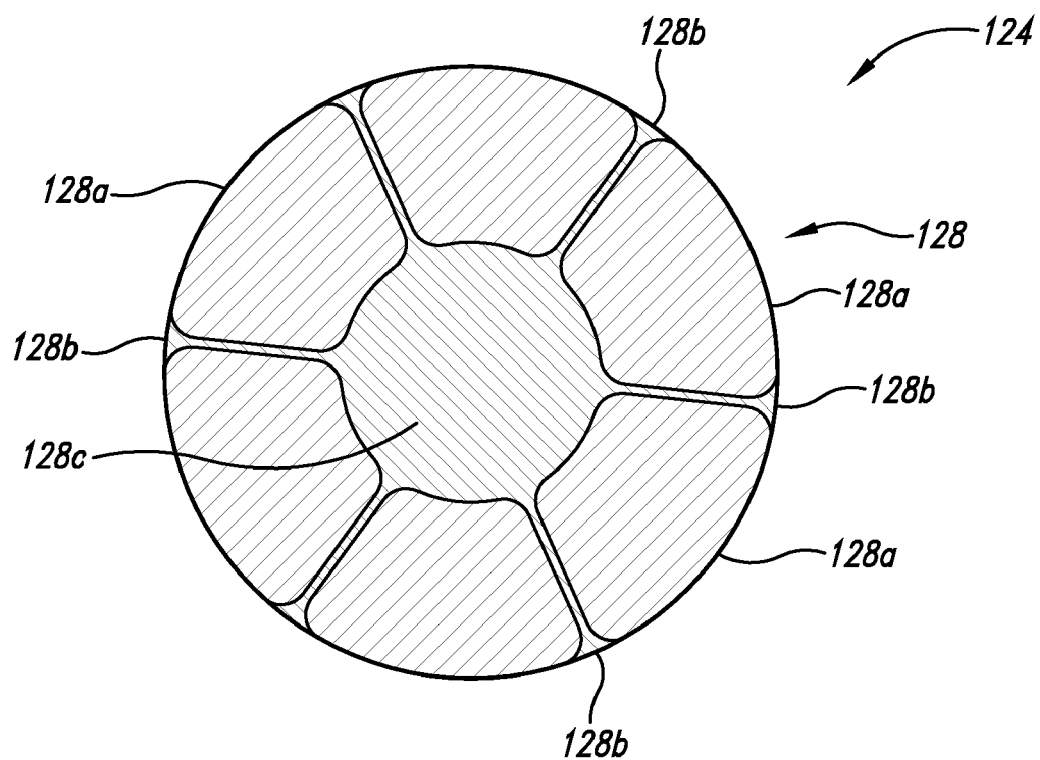
FIG. 4F is a sectional view of a solid conductor and a stranded support structure as a coaxial set.
Figure 4G:
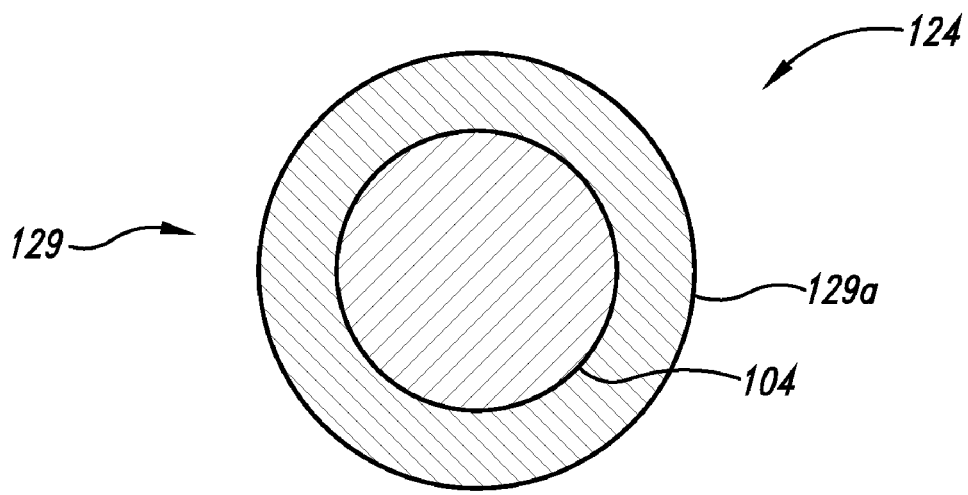
FIG. 4G is a sectional view of a conductor as a coaxial set.
Figure 4H:
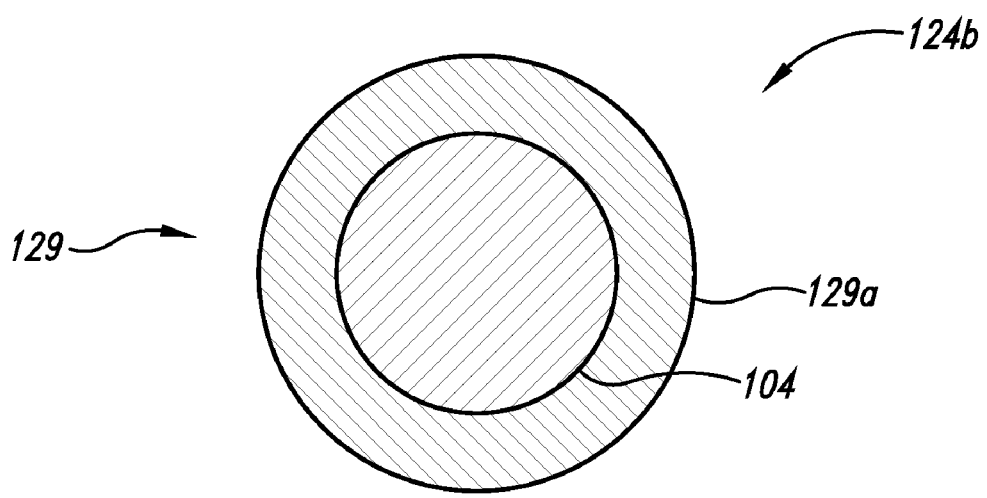
FIG. 4H is a sectional view of a conductor as a coaxial set.

In other implementations, each of the elongated conductive members 124 can be versions of the coaxial set 102 as shown in FIG. 4E. In alternative implementations, as shown in FIG. 4F, each of the elongated conductive members 124 can be from a drawn brazed strand (DBS) 128 with strands 128a made from a fatigue-resistant alloy, and braze 128b and center core 128c made from a conductive material such as silver or other highly conductive material. Further implementations include the elongated conductive member 124 as a coaxial set 129, as shown in FIG. 4G, with a tubular support structure 129a (such as a DFT) made from material other than the p/s elastic material (such as MP35N or other fatigue resistant alloy). The tubular structure 128a of the coaxial set 128 can be filled with the conductive core 104. Other implementations of the stranded conductor 124b can be made with versions of the coaxial set 129 as shown in FIG. 4H.

Since Nitinol and MP35N are far more resistive than either silver or copper, in some implementations with portions of the tubular support structure 106 being made from Nitinol or the tubular support structure 129a made from MP35N and the conductive core 104 being made from a metal such as silver or copper, most of the electrical current will flow through the conductive core rather than the tubular support structure. Although highly fatigue-resistant composite wires such as MP35N DFT and DBS, when filled with a highly conductive metal such as silver, exhibit excellent electrical conductivity, they do not exhibit the superelastic properties or the shape memory properties of Nitinol.

Nitinol DFT, MP35N DFT, and DBS composite wires are commercially available with core cross-sections ranging from about 15% to 41% of the total area. Even with a 15% cross-section dedicated for the conductive core 104, with many of the constructions, a majority of electrical current would flow through a low resistivity conductive core, such as made from silver, copper, or gold. In some applications, a material for the conductive core 104 is chosen due to its enhanced radiopaque properties which result from the atomic number and mass density of the core metal. For example, gold offers higher radiopacity than silver or copper, while retaining relatively low resistivity.

Figure 5:
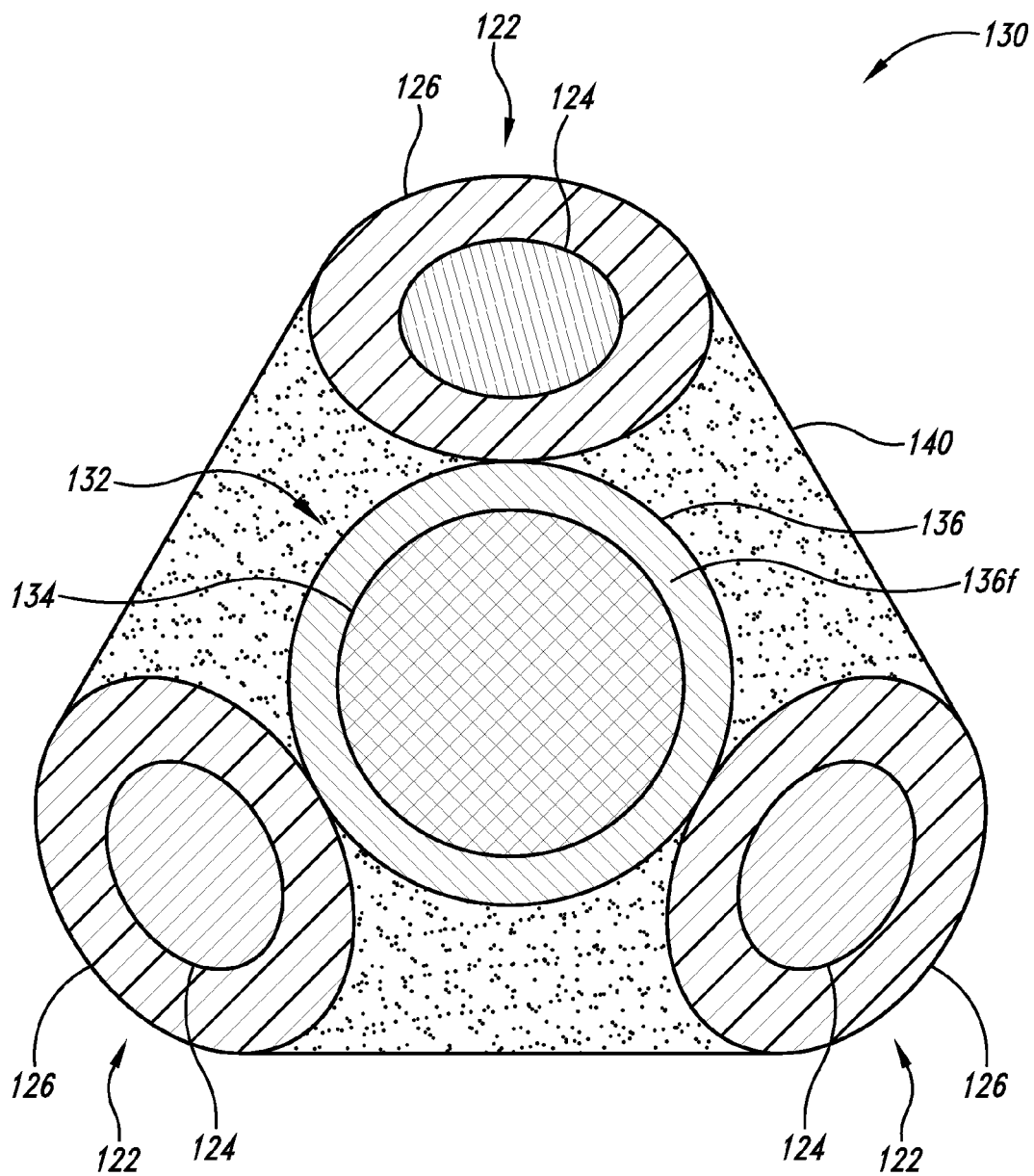
FIG. 5 is a sectional view of a fifth implementation of the enhanced implantable antenna system using a backbone support structure with a triangular sectional shape.

A fifth implementation 130 of the enhanced implantable antenna system is sectionally shown in FIG. 5 as having a backbone support structure 132 including a p/s elastic core 134, encased in a sleeve 136. In some implementations the p/s elastic core 134 is made from shape-set Nitinol and the sleeve 136 is made from a polymer such as PTFE, FEP, PFA, ETFE, PVDF, PEEK, LDPE, HDPE, polyurethane, silicone, or blends or alloys of these materials. The fifth implementation 130 further includes three of the insulated conductors 122 all of which are encased along with the backbone support structure 132 in an electrical insulator 140.

Figure 5A:
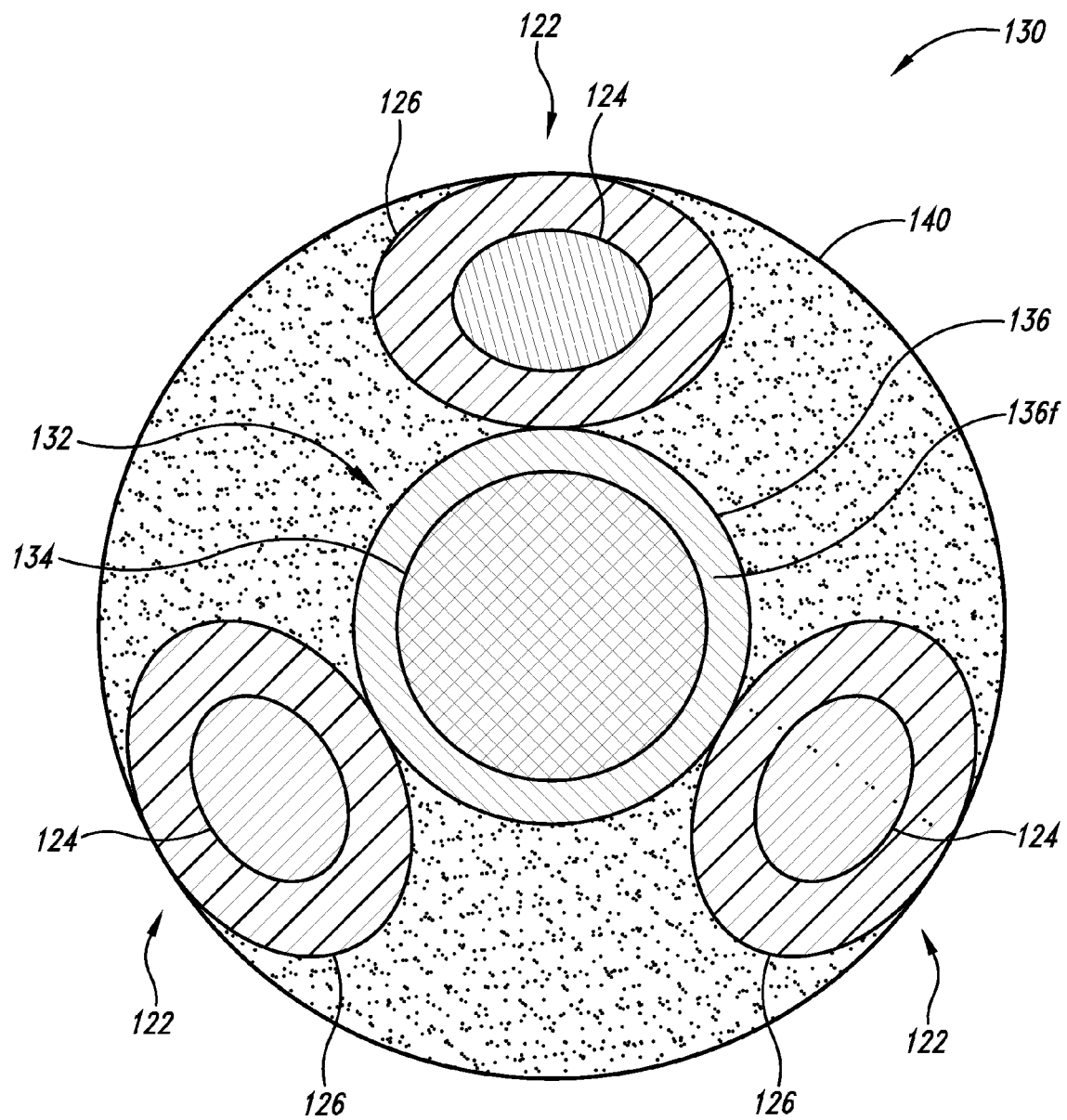
FIG. 5A is a sectional view of a fifth implementation of the enhanced implantable antenna system using a backbone support structure with a circular sectional shape.

Each of the three insulated conductors 122 each occupy a corner position of a triangular configuration of the insulator 140 in one implementation as shown in FIG. 5, and has a circular sectional shape of the insulator 140 in another implementation as shown in FIG. 5A. In some implementations the backbone support structure 132 is used solely for structural support to provide shape enhancement whereas in other implementations, in addition to structural support, the backbone support structure also provides antenna functionality. In both FIGS. 5 and 5A, the insulated conductors 122 are drawn as ellipses to illustrate that they can be helically wound around the backbone support structure 132. The form of the helix can range from zero to a plurality of turns per unit length, as required for a specific application.

Figure 6:
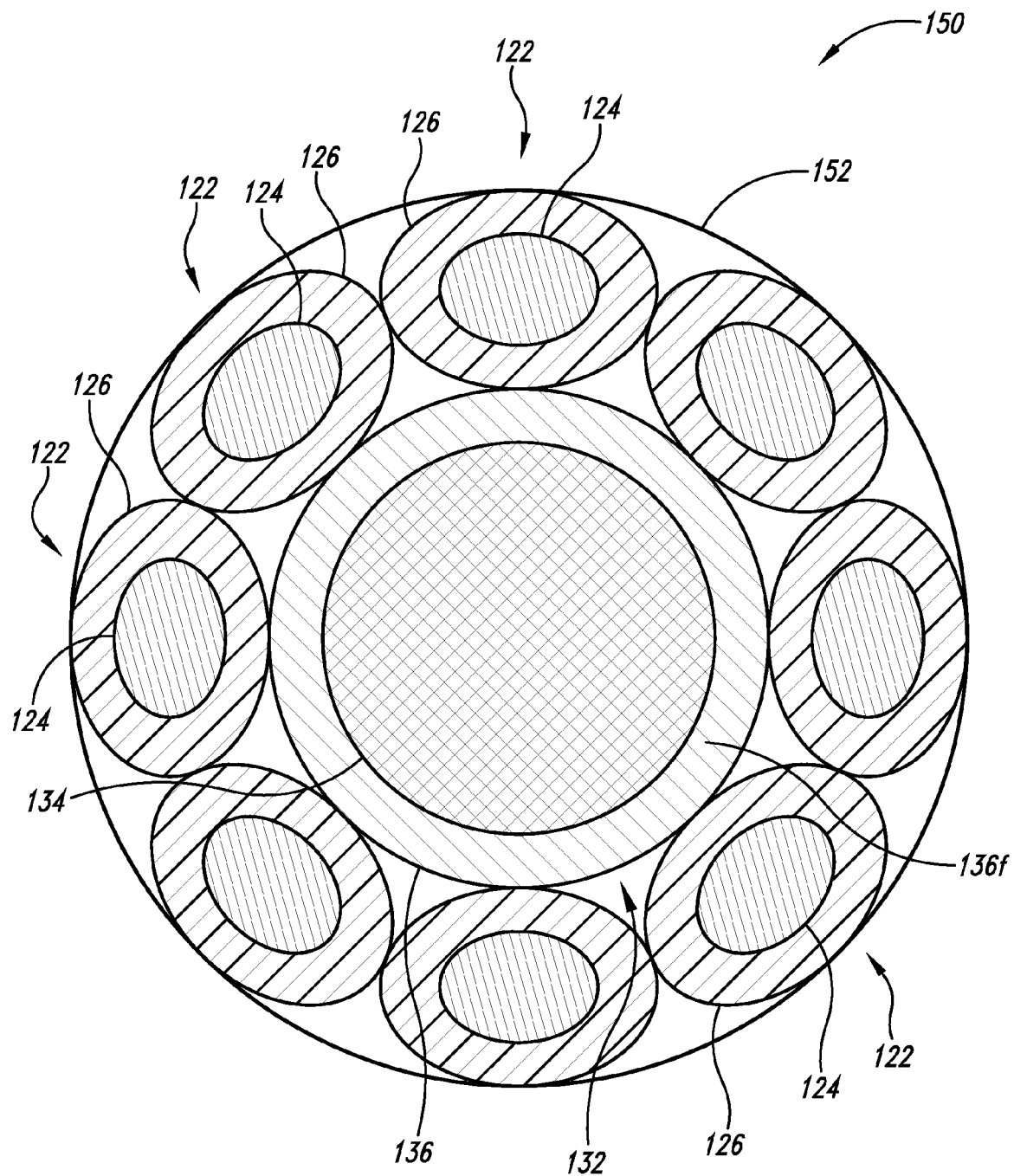
FIG. 6 is a sectional view of a sixth implementation of the enhanced implantable antenna system using at least the backbone support structure.

A sixth implementation 150 of the enhanced implantable antenna system is sectionally shown in FIG. 6 as having the backbone support structure 132 surrounded by eight of the insulated conductors 122 and all encased in an insulator 152.

Figure 7:
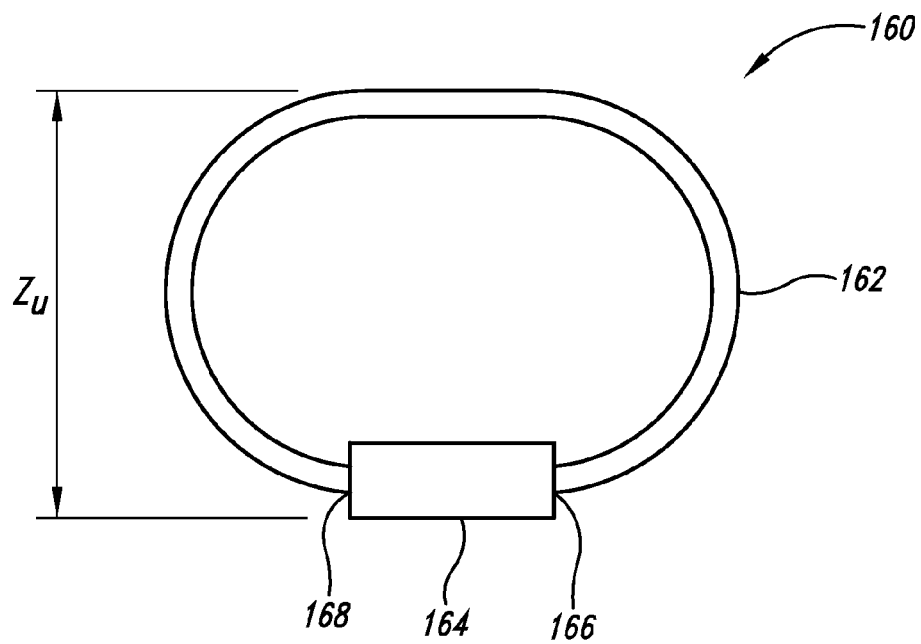
FIG. 7 is a side-elevational schematic of a first implant having an inductive H-field loop antenna in an uncompressed state using aspects of an enhanced implantable antenna system and method and coupled to an electronic enclosure.
Figure 8:
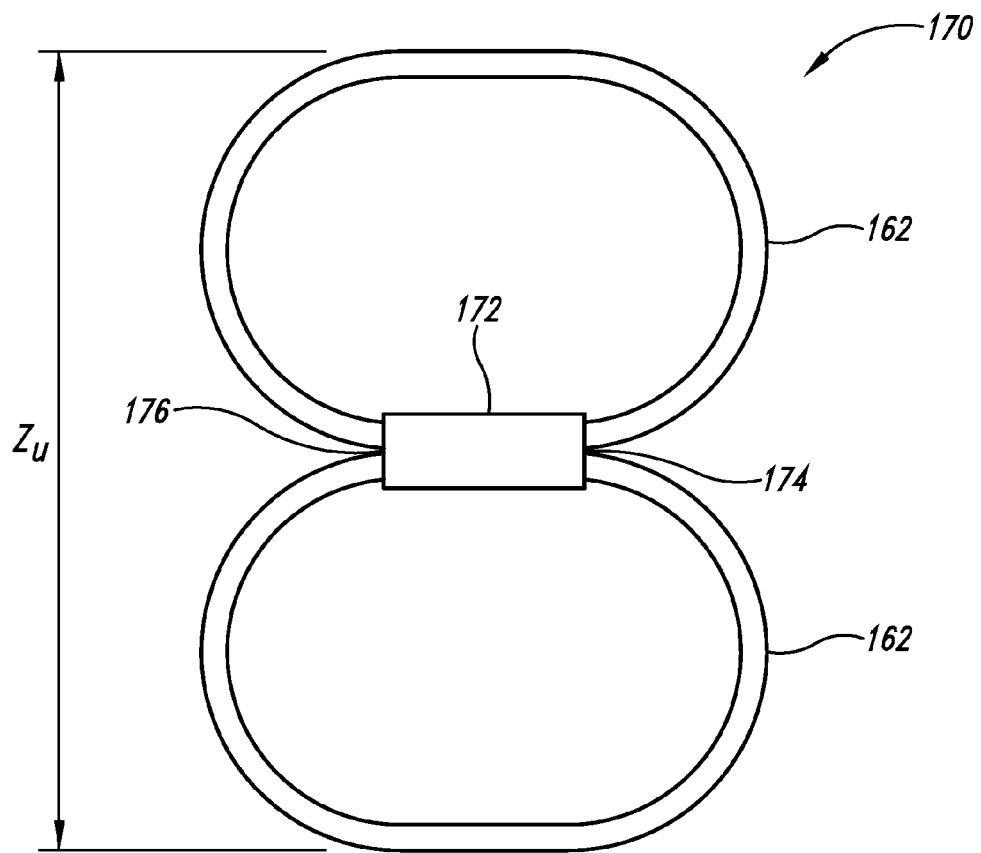
FIG. 8 is a side-elevational schematic of a second implant in an uncompressed state having two of the inductive (H-field) loop antennas of FIG. 1 coupled to an electronic enclosure.
Figure 9:
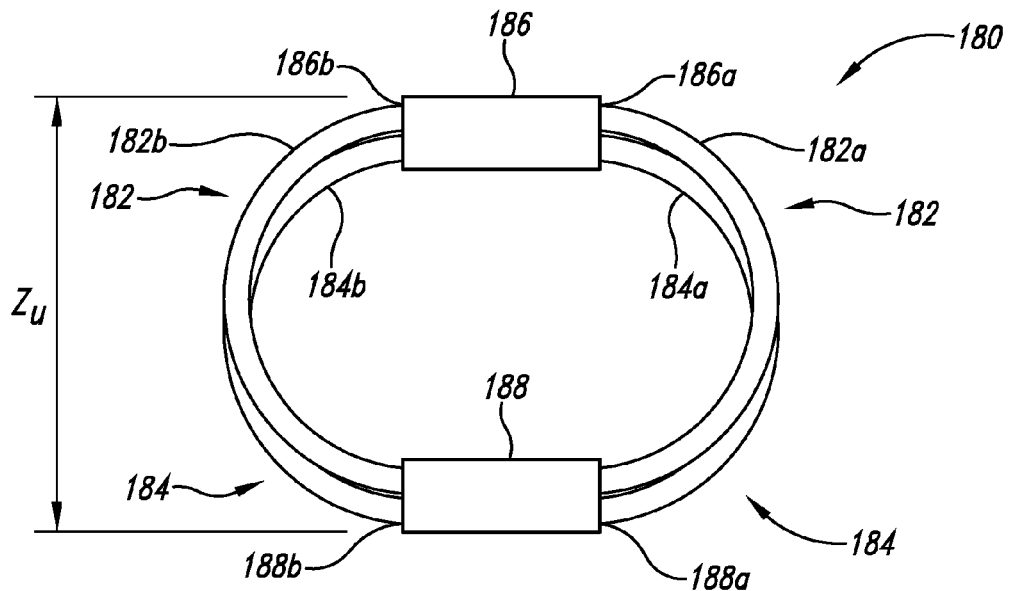
FIG. 9 is a side-elevational schematic of a third implant having two of the inductive (H-field) loop antennas of FIG. 1 in an uncompressed state coupled to two electronic enclosures.

FIGS. 7-11 show representative versions of implants that incorporate the enhanced implantable antenna system including the implementations depicted above. In FIGS. 1-3 and 7-11, the implantable antenna system may be used for inbound power delivery to the implant, inbound signal communication to the implant, and/or outbound signal communication to an external system. In FIGS. 7-9, implants with versions of the implantable antenna system with inductive loop antennas are shown, which can have one or multiple turns of any one of the implementations described above.

Figure 7A:
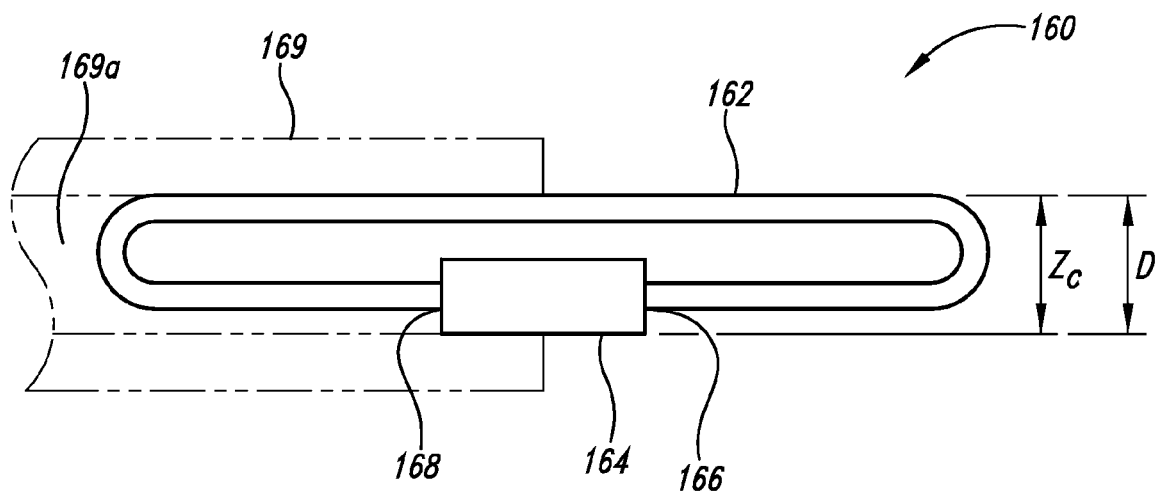
FIG. 7A is a side-elevational schematic of the first implant having an inductive H-field loop antenna in a compressed state using aspects of the enhanced implantable antenna system and method and coupled to the electronic enclosure.

A first implant version 160 is shown in FIG. 7 to include an inductive H-field loop antenna 162 coupled with an electronic enclosure 164 on a first side 166 and a second side 168 of the electronic enclosure. The first implant version 160 is shown in FIG. 7 as being in an uncompressed state having a measurement of Zu along a first dimension and is shown in FIG. 7A as being in a compressed state having a measurement of Zc along the first dimension to be fitted into a delivery tubular structure 169 having an interior 169a with an internal diameter, D. In some implementations, the ratio between Zu and Zc is at least 3:1 and in other implementations at least 5:1. The loop antenna 162 includes one or more electrical conductors and one or more mechanical elements such as found in the depicted implementations described above or with other implementations using aspects of the enhanced implantable antenna system.

Figure 8A:
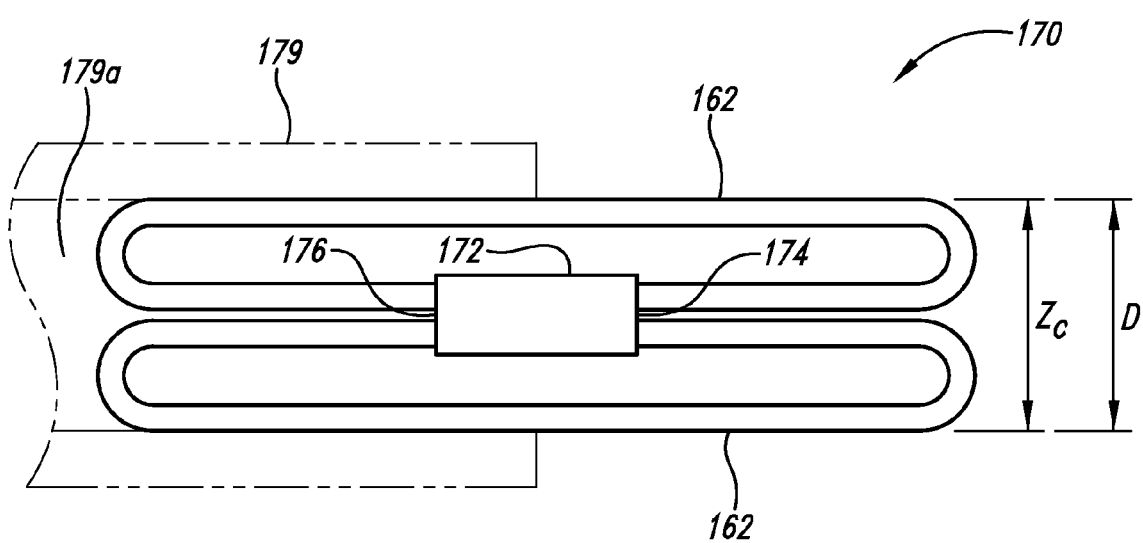
FIG. 8A is a side-elevational schematic of the second implant in a compressed state having two of the inductive (H-field) loop antennas of FIG. 1 coupled to the electronic enclosure.

A second implant version 170 is shown in FIG. 8 to include two of the inductive (H-field) loop antennas 162 both coupled to an electronic enclosure 172 on a first side 174 and a second side 176. The second implant version 170 is shown in FIG. 8 as being in an uncompressed state having a measurement of Zu along a first dimension and is shown in FIG. 8A as being in a compressed state having a measurement of Zc along the first dimension to be fitted into a delivery tubular structure 179 having an interior 179a with an internal diameter, D. In some implementations, the ratio between Zu and Zc is at least 3:1 and in other implementations at least 5:1. The two loop antennas 162 provide additional area for transmitting or receiving magnetic field signals, and they provide an alternate mechanical shape for anchoring the device in an anatomic location. Having two of the loop antennas 162 to the second implant version 170 for inbound power, inbound communications, or outbound communications provide added power and/or signal strength for inbound power or communication and added signal strength and/or field shaping for outbound communication. These loop antennas need not reside in the same plane.

Figure 9A:
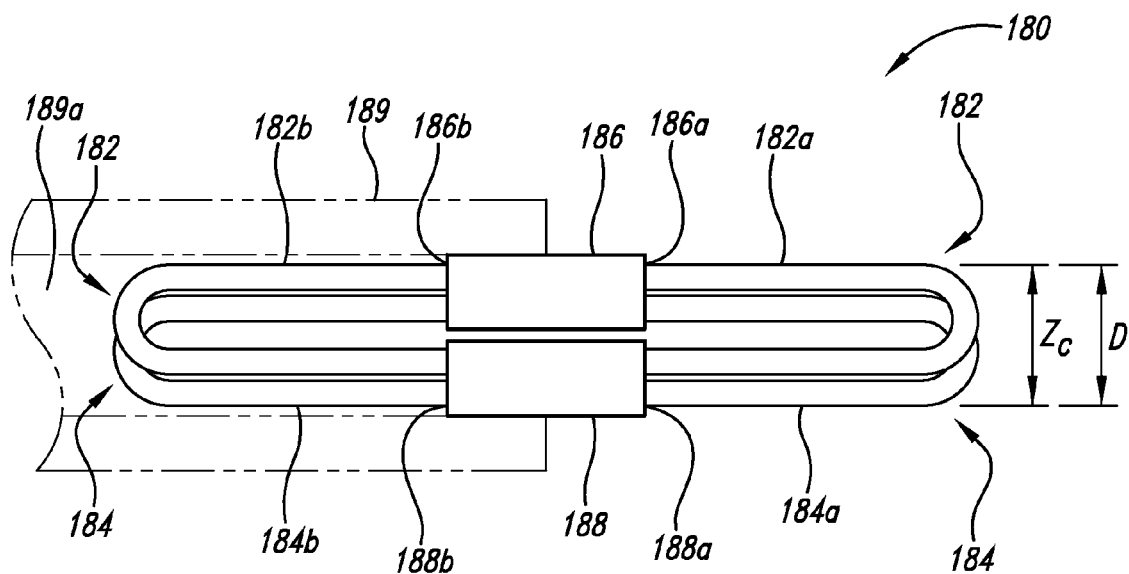
FIG. 9A is a side-elevational schematic of the third implant having two of the inductive (H-field) loop antennas of FIG. 1 in a compressed state coupled to two electronic enclosures.

A third implant version 180 is shown in FIG. 9 to include a first inductive (H-field) loop antenna 182 (having a first portion 182a and a second portion 182b) and a second inductive (H-field) loop antenna 184 having a first portion 184a and a second portion 184b) both coupled to a first electronic enclosure 186 (having a first side 186a and a second side 186b) and a second electronic enclosure 188 (having a first side 188a and a second side 188b). The third implant version 180 is shown in FIG. 9 as being in an uncompressed state having a measurement of Zu along a first dimension and is shown in FIG. 9A as being in a compressed state having a measurement of Zc along the first dimension to be fitted into a delivery tubular structure 189 having an interior 189a with an internal diameter, D. In some implementations, the ratio between Zu and Zc is at least 3:1 and in other implementations at least 5:1.

The first portion 182a of the first loop antenna 182 and the first portion 184a of the second loop antenna 184 both extend between the first side 186a of the first electronic enclosure 186 and the first side 188a of the second electronic enclosure 188. The second portion 182b of the first loop antenna 182 and the second portion 184b of the second loop antenna 184 both extend between the second side 186b of the first electronic enclosure 186 and the second side 188b of the second electronic enclosure 188.

The third implant version 180 has advantages associated with two loop antennas similar to the second implant version 170 and provides an alternative shape for anchoring in an anatomic location. The third implant version 180 also has the additional space for electronic components associated with a second electronic enclosure, namely, the second electronic enclosure 188 spaced apart from the first electronic enclosure 186.

Figure 10:
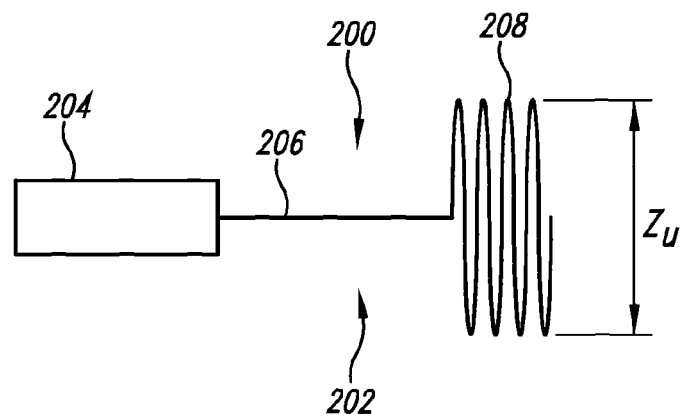
FIG. 10 is a side-elevational schematic of a fourth implant in an uncompressed state having an electrical E-field antenna using aspects of the enhanced implantable antenna system and method and coupled to an electronic enclosure.

A fourth implant version 200 as shown in FIG. 10 has an electrical E-field antenna 202 coupled to an electronic enclosure 204. The E-field antenna 202 has an elongated member 206 coupled to the electronic enclosure 204 and extending therefrom. Coupled with the elongated member 206 as also included with the E-field antenna 202, is a helical coil section 208, which can be threaded into tissue to provide a mechanical anchor for the fourth implant version 200.

Figure 10A:
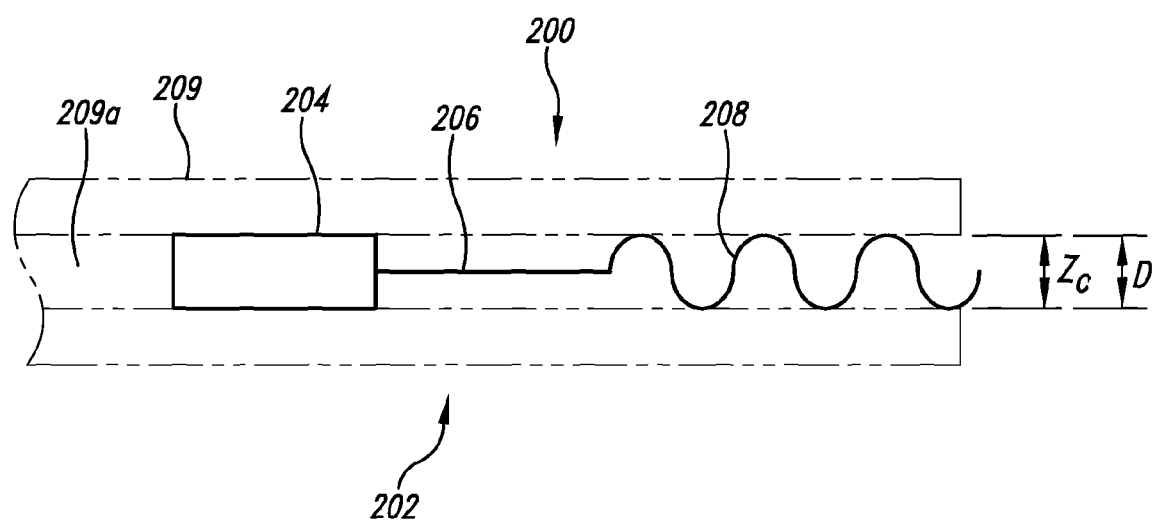
FIG. 10A is a side-elevational schematic of the fourth implant in a compressed state having an electrical E-field antenna using aspects of the enhanced implantable antenna system and method and coupled to an electronic enclosure.

The fourth implant version 200 is shown in FIG. 10 as being in an uncompressed state with the helical coil section 208 having a measurement of Zu along a first dimension and is shown in FIG. 10A as being in a compressed state with the helical coil section having a measurement of Zc along the first dimension to be fitted into the delivery tubular structure 209 having an interior 209a with an internal diameter, D. In some implementations, the ratio between Zu and Zc is at least 3:1 and in other implementations at least 5:1. The electronic enclosure 204 of the fourth implant version 200 can be either in electrical or capacitive contact with surrounding tissue and would act as a local electrical ground reference. Given this arrangement, an E-field could be produced (for outbound signaling) or sensed (for inbound power delivery or signaling) between the electronic enclosure 204 and the E-field antenna 202.

Figure 11:
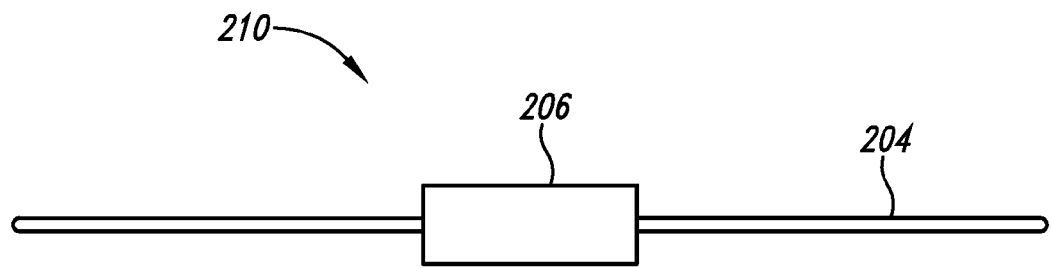
FIG. 11 is a side-elevational schematic of a fifth implant having two electrical E-field antennas using aspects of the enhanced implantable antenna system and method and coupled to an electronic enclosure.
Figure 11A:
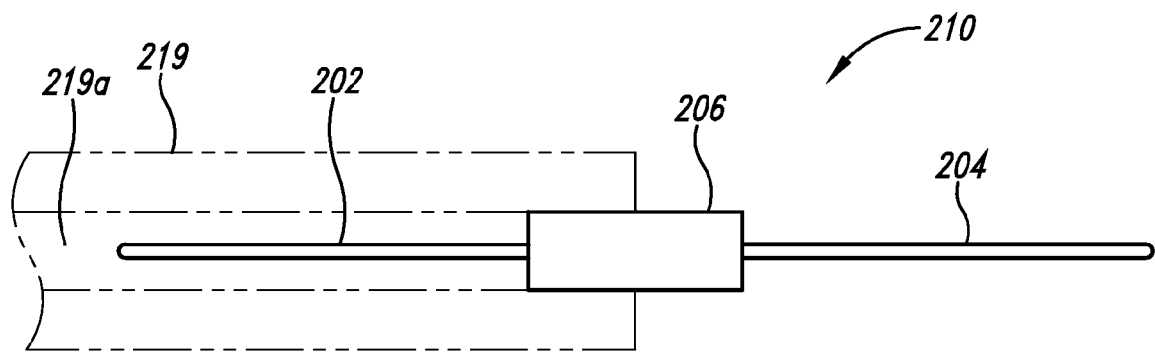
FIG. 11A is a side-elevational schematic of the fifth implant being inserted into a tubular structure.

A fifth implant version 210 as shown in FIG. 11 has a first electrical E-field antenna 202 and a second electrical E-field antenna 204 both coupled to either end of an electronic enclosure 206. The first E-field antenna 202 and the second E-field antenna 204 are both configured as straight sections which can be inserted into soft tissue to provide a mechanical anchor. In the fifth implant version 210, the electronic enclosure 206 can be insulated from adjacent areas of tissue having received implantation of the fifth implant version. An E-field could be produced (for outbound signaling) or sensed (for inbound power delivery or signaling) between the first E-field antenna 202 and the second E-field antenna 204 as a dipole antenna. FIG. 11A shows the fifth implant being inserted into a tubular structure 219.

From the foregoing it will be appreciated that, although specific embodiments of the invention have been described herein for purposes of illustration, various modifications may be made without deviating from the spirit and scope of the invention. Accordingly, the invention is not limited except as by the appended aspects.

ASPECTS

1. For implantation through a tubular structure into a biological structure, a system comprising:
   an electronic device;
   an antenna electrically coupled to the electronic device, at least a portion of the antenna being helical, the helical portion of the antenna having a uncompressed state with a measurement, Zu, along a first dimension and a compressed state with a measurement, Zc, along the first dimension.

2. The system of aspect 1 wherein the helical antenna portion includes:
   a p/s elastic structure;
   an electrically conductive structure coupled with the p/s elastic structure; and
   an electrical insulator coupled with the p/s elastic structure.

3. The helical antenna portion of aspect 2 wherein the p/s elastic structure is a p/s elastic tubular structure.

4. The helical antenna portion of aspect 3 wherein the electrically conductive structure fills the p/s elastic tubular structure.

5. The helical antenna portion of aspect 3 wherein the p/s elastic structure is a drawn filled tube.

6. The helical antenna portion of aspect 5 wherein the electrically conductive structure serves as filling material for the p/s elastic structure as the drawn filled tube.

7. The helical antenna portion of aspect 2 wherein the p/s elastic structure is made from a material that is pseudoelastic in a temperature range of at least 33 degrees Celsius to 43 degrees Celsius.

8. The helical antenna portion of aspect 7 wherein the p/s elastic structure is made from a material that is pseudoelastic in a temperature range of at least 0 degrees Celsius to 100 degrees Celsius.

9. The helical antenna portion of aspect 2 wherein the p/s elastic structure is made from a material that is superelastic in a temperature range of at least 33 degrees Celsius to 43 degrees Celsius.

10. The helical antenna portion of aspect 9 wherein the p/s elastic structure is made from a material that is superelastic in a temperature range of at least 0 degrees Celsius to 100 degrees Celsius.

11. The helical antenna portion of aspect 2 wherein the p/s elastic structure is made from a nickel-titanium alloy.

12. The helical antenna portion of aspect 11 wherein the p/s elastic structure is made from Nitinol.

13. The helical antenna portion of aspect 12 wherein the electrically conductive has a higher electrical conductivity than Nitinol.

14. The helical antenna portion of aspect 2 wherein the p/s elastic structure is made from a metal.

15. The helical antenna portion of aspect 2 wherein the p/s elastic structure is made from a polymer.

16. The helical antenna portion of aspect 2 wherein the electrically conductive structure is of at least one of the following materials: silver, copper, gold, aluminum, iridium, brass, nickel, platinum.

17. The helical antenna portion of aspect 2 wherein the p/s elastic structure is in an austenitic phase in at least a temperature range between 33 degrees Celsius and 43 degrees Celsius.

18. The helical antenna portion of aspect 2 wherein the p/s elastic structure is shaped set with shape memory properties to maintain a desired shape in a temperature range of at least between 33 degrees Celsius and 43 degrees Celsius.

19. The helical antenna portion of aspect 2 wherein the p/s elastic structure has an elastic strain range of at least 3% in a temperature range of at least between 33 degrees Celsius and 43 degrees Celsius.

20. The helical antenna portion of aspect 19 wherein the p/s elastic structure has an elastic strain range of at least 6% in a temperature range of at least between 33 degrees Celsius and 43 degrees Celsius.

21. The helical antenna portion of aspect 19 wherein the p/s elastic structure has an elastic strain range of at least 3% in a temperature range of at least between 0 degrees Celsius and 100 degrees Celsius.

22. The helical antenna portion of aspect 19 wherein the p/s elastic structure has an elastic strain range of at least 6% in a temperature range of at least between 0 degrees Celsius and 100 degrees Celsius.

23. The helical antenna portion of aspect 1 wherein the ratio of Zu to Zc is at least 3:1.

24. The helical antenna portion of aspect 23 wherein the ratio of Zu to Zc is at least 5:1.

25. The helical antenna portion of aspect 1 wherein the measurement of Zc is an internal diameter of a catheter.

26. The helical antenna portion of aspect 1 wherein the measurement of Zc is an internal diameter of a cannula.

27. The helical antenna portion of aspect 26 wherein the helical antenna portion has a fatigue life of at least 1,000,000 cycles in a temperature range of at least between 33 degrees Celsius and 43 degrees Celsius.

28. The helical antenna portion of aspect 27 wherein the helical antenna portion has a fatigue life of at least 10,000,000 cycles in a temperature range of at least between 33 degrees Celsius and 43 degrees Celsius.

29. The helical antenna portion of aspect 28 wherein the helical antenna portion has a fatigue life of at least 100,000,000 cycles in a temperature range of at least between 33 degrees Celsius and 43 degrees Celsius.

30. The helical antenna portion of aspect 29 wherein the helical antenna portion has a fatigue life of at least 400,000,000 cycles in a temperature range of at least between 33 degrees Celsius and 43 degrees Celsius.

31. The helical antenna portion of aspect 26 wherein the helical antenna portion is shaped as a loop in a temperature range of at least between 33 degrees Celsius to 43 degrees Celsius.

32. The helical antenna portion of aspect 1 wherein the helical antenna portion is configured to receive electric fields for the electronic device.

33. The helical antenna portion of aspect 1 wherein the helical antenna portion is configured to transmit electric fields for the electronic device.

34. The helical antenna portion of aspect 33 wherein the biological structure is a blood vessel and the helical antenna portion is shaped and sized to be received by the blood vessel.

35. The helical antenna portion of aspect 33 wherein the p/s elastic structure extends along a central axis of the helical antenna portion.

36. The helical antenna portion of aspect 35 wherein electrically conductive structure extends along the central axis of the helical antenna portion.

37. The helical antenna portion of aspect 36 wherein the electrically conductive structure fills the p/s elastic structure along the central axis of the helical antenna portion.

38. The helical antenna portion of aspect 35 wherein the electrically conductive structure spirals around the p/s elastic structure.

39. The helical antenna portion of aspect 33 wherein the electrically conductive structure extends along the central axis of the helical antenna portion and the p/s elastic structure extends along another axis parallel with the central axis.

40. The helical antenna portion of aspect 33 wherein the electrically conductive structure is of a solid construction.

41. The helical antenna portion of aspect 33 wherein the electrically conductive structure is of a stranded construction.

42. The helical antenna portion of aspect 33 wherein the p/s elastic structure is of a solid construction.

43. The helical antenna portion of aspect 33 wherein the p/s elastic structure is of a stranded construction.

44. The helical antenna portion of aspect 33 wherein the p/s elastic structure is of a drawn brazed strand construction.

45. The helical antenna portion of aspect 33 wherein the p/s elastic structure is configured to be electrically coupled to an electronic device.

46. The helical antenna portion of aspect 33 wherein the electrically conductive structure is configured to be electrically coupled to an electronic device.

47. The helical antenna portion of aspect 46 wherein the p/s elastic structure is configured to be electrically insulated rather than being electrically coupled to the electronic device.

48. For implantation through a tubular structure into a biological structure, an antenna configured to electrically couple to an electronic device, at least a portion of the antenna being helical, the helical portion of the antenna having a uncompressed state with a measurement, Zu, along a first dimension and a compressed state with a measurement, Zc, along the first dimension, the helical antenna portion including:
  a plurality of p/s elastic structures;
  an electrically conductive structure coupled with the p/s elastic structure; and
  an electrical insulator coupled with at least one of the p/s elastic structures.

49. The helical antenna portion of aspect 48 further including a plurality of electrically conductive structures wherein each of the plurality of p/s elastic structures is tubular, each of the electrically conductive structures filling a different one of the p/s elastic structures.

50. The helical antenna portion of aspect 49 further including a plurality of electrical insulators, each electrical insulator of the plurality covering a different one of the plurality of the p/s elastic structures and the electrical insulator coupled with the plurality of the p/s elastic structures through the electrical insulator.

51. The helical antenna portion of aspect 48 wherein each of the plurality of p/s elastic structures is coupled to the electrical insulator, further including a plurality of electrically conductive structures coupled to the p/s elastic structures through the electrical insulator.

52. The helical antenna portion of aspect 51 further including a plurality of electrical insulators each covering a different one of the plurality of the electrically conductive structures.

53. The helical antenna portion of aspect 48 wherein the electrically conductive structure is configured for electrical coupling with an electronic device.

54. The helical antenna portion of aspect 53 wherein the electrically conductive structure is electrically isolated from the plurality of p/s elastic structures.

55. The helical antenna portion of aspect 54 wherein the electrically conductive structure is electrically isolated from the plurality of p/s elastic structures through the electrical insulator.

56. For implantation through a tubular structure into a biological structure, an antenna configured to electrically couple to an electronic device, at least a portion of the antenna being helical, the helical portion of the antenna having a uncompressed state with a measurement, Zu, along a first dimension and a compressed state with a measurement, Zc, along the first dimension, the helical antenna portion including:

a p/s elastic structure;

a plurality of electrically conductive structures coupled with the p/s elastic structure; and an electrical insulator coupled with the p/s elastic structure.

57. The helical antenna portion of aspect 56, further including a plurality of p/s elastic structures wherein one of the plurality of electrically conductive structures is coupled to the p/s elastic structure and the others of the plurality of electrically conductive structures are each directly coupled to a different one of the plurality of p/s elastic structures.

58. The helical antenna portion of aspect 57, further including a plurality of electrical insulators, each electrical insulator of the plurality covering a different one of the plurality of the electrically conductive structures.

59. The helical antenna portion of aspect 56 further including a plurality of p/s elastic structures coupled to the electrically conductive structures through the electrical insulator.

60. The helical antenna portion of aspect 56 further including a plurality of electrical insulators each covering a different one of the plurality of the electrically conductive structures.

61. The helical antenna portion of aspect 56 wherein each of the electrically conductive structures are configured for electrical coupling with an electronic device.

62. The helical antenna portion of aspect 56 wherein each of the electrically conductive structures are electrically isolated from the plurality of p/s elastic structures.

63. The helical antenna portion of aspect 56 wherein each of the electrically conductive structures are electrically isolated from the plurality of p/s elastic structures through the electrical insulator.

64. The helical antenna portion of aspect 56 wherein each of the electrically conductive structures spiral around the p/s elastic structure.

The invention is claimed is:

1. For implantation through a tubular structure into a biological structure, a system comprising:

an electronic device;

an antenna electrically coupled to the electronic device, at least a portion of the antenna being helical, the helical portion of the antenna having a uncompressed state with a measurement, Zu, along a first dimension and a compressed state with a measurement, Zc, along the first dimension, wherein the biologic structure is a blood vessel and wherein the helical antenna portion is shaped and sized to be implanted into the blood vessel.

2. The system of claim 1 wherein the helical antenna portion includes:

a p/s elastic structure;

an electrically conductive structure coupled with the p/s elastic structure; and an electrical insulator coupled with the p/s elastic structure.

3. The helical antenna portion of claim 2 wherein the p/s elastic structure is a p/s elastic tubular structure.

4. The helical antenna portion of claim 3 wherein the electrically conductive structure fills the p/s elastic tubular structure.

5. The helical antenna portion of claim 3 wherein the p/s elastic structure is a drawn filled tube.

6. The helical antenna portion of claim 5 wherein the electrically conductive structure serves as filling material for the p/s elastic structure as the drawn filled tube.

7. The helical antenna portion of claim 2 wherein the p/s elastic structure is made from a material that is pseudoelastic in a temperature range of at least 33 degrees Celsius to 43 degrees Celsius.

8. An apparatus adapted for implantation through a tubular structure into a biological structure, the apparatus comprising:

an antenna configured to electrically couple to an electronic device, at least a portion of the antenna being helical, the helical portion of the antenna having a uncompressed state with a measurement, Zu, along a first dimension and a compressed state with a measurement, Zc, along the first dimension, the helical antenna portion including:

a plurality of p/s elastic structures;

an electrically conductive structure coupled with the p/s elastic structure; and an electrical insulator coupled with at least one of the p/s elastic structures.

9. The helical antenna portion of claim 8 further including a plurality of electrically conductive structures wherein each of the plurality of p/s elastic structures is tubular, each of the electrically conductive structures filling a different one of the p/s elastic structures.

10. The helical antenna portion of claim 9 further including a plurality of electrical insulators, each electrical insulator of the plurality covering a different one of the plurality of the p/s elastic structures and the electrical insulator coupled with the plurality of the p/s elastic structures through the electrical insulator.

11. The helical antenna portion of claim 8 wherein each of the plurality of p/s elastic structures is coupled to the electrical insulator, further including a plurality of electrically conductive structures coupled to the p/s elastic structures through the electrical insulator.

12. The helical antenna portion of claim 11 further including a plurality of electrical insulators each covering a different one of the plurality of the electrically conductive structures.

13. The helical antenna portion of claim 8 wherein the electrically conductive structure is configured for electrical coupling with an electronic device.

14. The helical antenna portion of claim 13 wherein the electrically conductive structure is electrically isolated from the plurality of p/s elastic structures.

15. An apparatus adapted for implantation through a tubular structure into a biological structure, the apparatus comprising:

an antenna configured to electrically couple to an electronic device, at least a portion of the antenna being helical, the helical portion of the antenna having a uncompressed state with a measurement, Zu, along a first dimension and a compressed state with a measurement, Zc, along the first dimension, the helical antenna portion including:

a p/s elastic structure;

a plurality of electrically conductive structures coupled with the p/s elastic structure; and an electrical insulator coupled with the p/s elastic structure.

16. The helical antenna portion of claim 15, further including a plurality of p/s elastic structures wherein one of the plurality of electrically conductive structures is coupled to the p/s elastic structure and the others of the plurality of electrically conductive structures are each directly coupled to a different one of the plurality of p/s elastic structures.

17. The helical antenna portion of claim 16, further including a plurality of electrical insulators, each electrical insulator of the plurality covering a different one of the plurality of the electrically conductive structures.

18. The helical antenna portion of claim 15 further including a plurality of p/s elastic structures coupled to the electrically conductive structures through the electrical insulator.

19. The helical antenna portion of claim 15 further including a plurality of electrical insulators each covering a different one of the plurality of the electrically conductive structures.

20. The helical antenna portion of claim 15 wherein each of the electrically conductive structures are configured for electrical coupling with an electronic device.

* * * * *